(12) United States Patent
Shin (10) Patent No.: US 9,668,853 B2
(45) Date of Patent: Jun. 6, 2017

(54) STENT FOR CONNECTING ADJACENT TISSUES OF ORGANS

(75) Inventor: Kyong-Min Shin, Seoul (KR)

(73) Assignees: TAEWOONG MEDICAL CO., LTD., Kyunggi-do (KR); Kyong-Min Shin, Seoul (KR)

(*) Notice: Subject to any disclaimer, the term of this patent is extended or adjusted under 35 U.S.C. 154(b) by 0 days.

(21) Appl. No.: 13/542,412

(22) Filed: Jul. 5, 2012

(65) Prior Publication Data
US 2013/0012969 A1 Jan. 10, 2013

(30) Foreign Application Priority Data
Jul. 6, 2011 (KR) .................. 10-2011-0066965

(51) Int. Cl.
| | | |
|---|---|---|
| *A61B 17/11* | (2006.01) | |
| *A61F 2/06* | (2013.01) | |
| *A61B 17/00* | (2006.01) | |
| *A61F 2/90* | (2013.01) | |

(52) U.S. Cl.
CPC .............. *A61F 2/064* (2013.01); *A61B 17/11* (2013.01); *A61B 17/1114* (2013.01); *A61B 2017/00862* (2013.01); *A61B 2017/00867* (2013.01); *A61B 2017/00995* (2013.01); *A61B 2017/1139* (2013.01); *A61F 2/90* (2013.01)

(58) Field of Classification Search
CPC .............. A61B 17/11; A61B 17/1114; A61B 2017/1107; A61B 2017/00995; A61B 2017/00867; A61B 2017/1139; A61B 2017/00862; A61F 2/90
USPC .............. 606/151, 153, 213, 216; 600/37; 623/2.14, 2.36
See application file for complete search history.

(56) References Cited

U.S. PATENT DOCUMENTS

| | | | | |
|---|---|---|---|---|
| 5,846,261 | A | * 12/1998 | Kotula et al. | 606/213 |
| 6,468,303 | B1 | * 10/2002 | Amplatz et al. | 623/1.2 |
| 6,668,197 | B1 | 12/2003 | Habib et al. | |
| 6,682,480 | B1 | 1/2004 | Habib et al. | |
| 7,780,686 | B2 | * 8/2010 | Park et al. | 606/153 |

(Continued)

FOREIGN PATENT DOCUMENTS

KR 100929242 12/2009

OTHER PUBLICATIONS

Notice of Allowance issued by the Korean Intellectual Property Office on Aug. 20, 2013.

*Primary Examiner* — Anh Dang
(74) *Attorney, Agent, or Firm* — IP & T Group LLP (57) ABSTRACT

Disclosed herein is a stent for connecting adjacent tissues of the organs of a patient. The stent includes a hollow cylindrical body which is formed by weaving a superelastic shape-memory alloy wire in an overlapping manner such that rhombic openings are formed, and wing parts which are provided by expanding respective opposite ends of the hollow cylindrical body outwards and turning the opposite ends inside out on bent portions. The wing parts face each other so that the wing parts are tensed in a longitudinal direction of the cylindrical body. Thereby, the wing parts can elastically move inwards or outwards with respect to the longitudinal direction to automatically adjust a distance between the wing parts in response to the distance between the adjacent tissues of the organs or thicknesses of walls of the organs, so that the wing parts are put into close contact with the adjacent tissues.

6 Claims, 11 Drawing Sheets

(56) References Cited

U.S. PATENT DOCUMENTS

| | | |
|---|---|---|
| 7,998,128 B2 | 8/2011 | Poston et al. |
| 2002/0188170 A1* | 12/2002 | Santamore ....... A61B 17/00234 600/37 |
| 2009/0281557 A1 | 11/2009 | Sander et al. |
| 2010/0174312 A1* | 7/2010 | Maahs et al. ................. 606/213 |

* cited by examiner

STENT FOR CONNECTING ADJACENT TISSUES OF ORGANS

CROSS-REFERENCE TO RELATED APPLICATIONS

The present application claims priority of Korean Patent Application No. 10-2011-0066965, filed on Jul. 6, 2011, which is incorporated herein by reference in its entirety.

BACKGROUND OF THE INVENTION

1. Field of the Invention

The present invention relates generally to a connection stent which connects the adjacent tissue of organs, such as the gall bladder, the pancreas, etc., of a patient so that the organs communicate with each other via the stent, thus forming a passage for an endoscopic operation, discharge or the shunting of bile or the like and, more particularly, to a stent for connecting adjacent tissues of the organs of a patient which includes a hollow cylindrical body ft/wed by weaving a superelastic shape-memory alloy wire in an overlapping manner, and wing parts provided by expanding respective opposite ends of the hollow cylindrical body outwards and turning the opposite ends inside out on bent portions so that the wing parts face each other so that they apply tension in a longitudinal direction of the hollow cylindrical body, whereby the wing parts elastically move inwards or outwards with respect to the longitudinal direction to automatically adjust the distance between the wing parts in response to the distance between the adjacent tissues of the organs or the thicknesses of walls of the organs and come into close contact with the adjacent tissues of the organs, so that the stent can be used regardless of the distance between the adjacent tissues of the organs or the thickness of tissue, and which can ensure not only the fixation of the stent to the organs but a seal that prevents leaks.

2. Description of the Related Art

Generally, stents are inserted into the internal organs, such as the gullet, stomach, duodenum, intestines, etc., of patients, thus forming passages.

Such a stent includes a hollow cylindrical body which is formed by weaving a superelastic shape-memory alloy wire in an overlapping manner such that a plurality of rhombic openings are formed in the hollow cylindrical body. Because the hollow cylindrical body can elastically expand and contract in the radial direction, when the stent is inserted into the internal organ of a patient, it can define a passage in the internal organ.

Recently, connection stents are used to allow access to an internal organ, such as the gall bladder or the pancreas, where it is difficult to directly conduct an endoscopic operation or an operation of discharging or shunting bile or the like.

That is, after piercing the adjacent tissues of the organs, such as the gall bladder, the pancreas, etc., a stent is inserted into the pierced holes so that the organs can communicate with each other.

Figure 1:
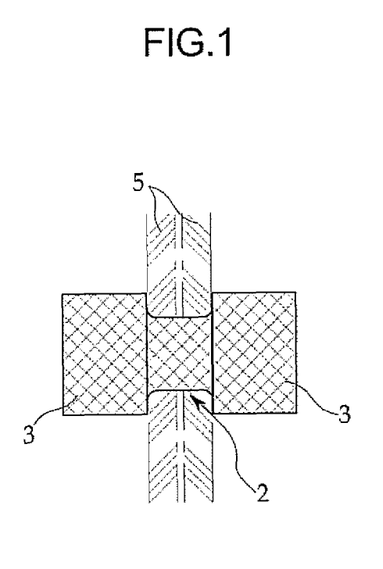
FIG. 1 is a side view showing a conventional connection stent.

FIG. 1 illustrates a conventional connection stent which was proposed in U.S. Pat. No. 6,620,122. As shown in FIG. 1, the conventional connection stent includes a hollow cylindrical body 2 which is formed by weaving a superelastic shape-memory alloy wire in an overlapping manner, and increased diameter parts 3 which are provided on opposite ends of the hollow cylindrical body 2 and have the shape of a dumbbell. After holes are formed through adjacent tissues 5 of the organs of a patient, the stent is inserted into the holes such that the increased diameter parts 3 are locked to the tissues 5 to prevent the stent from being removed therefrom, thus connecting the organs to each other.

However, the conventional connection stent is problematic in that the increased diameter parts 3 that are provided on the opposite ends of the hollow cylindrical body 2 make it difficult to insert the stent into the holes made in the tissues.

In addition, the distance between the increased diameter parts is fixed after the stent has been manufactured. Thus, when manufacturing the stent, the distance between adjacent tissues or the thicknesses of walls of the tissues must be taken into account. The stent may not be brought into elastic contact with the tissues, thus causing a gap between the stent and the tissue, making the discharge or shunting of bile or the like difficult.

Each edge of the increased diameter parts forms a right angle. This may damage the tissues of the organs.

Figure 2:
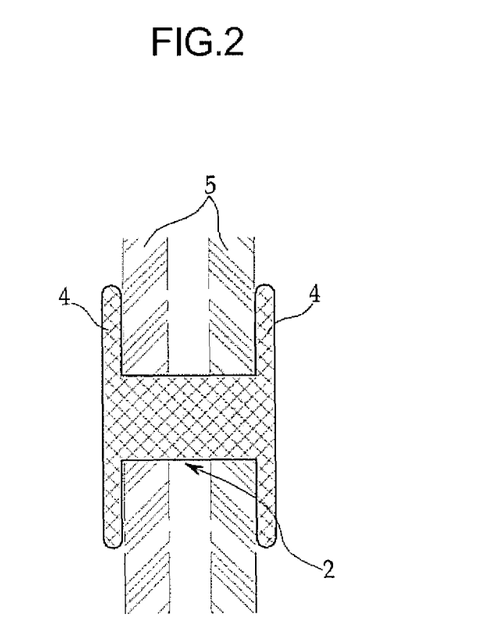
FIG. 2 is a side view showing another example of the conventional connection stent.
Figure 3:
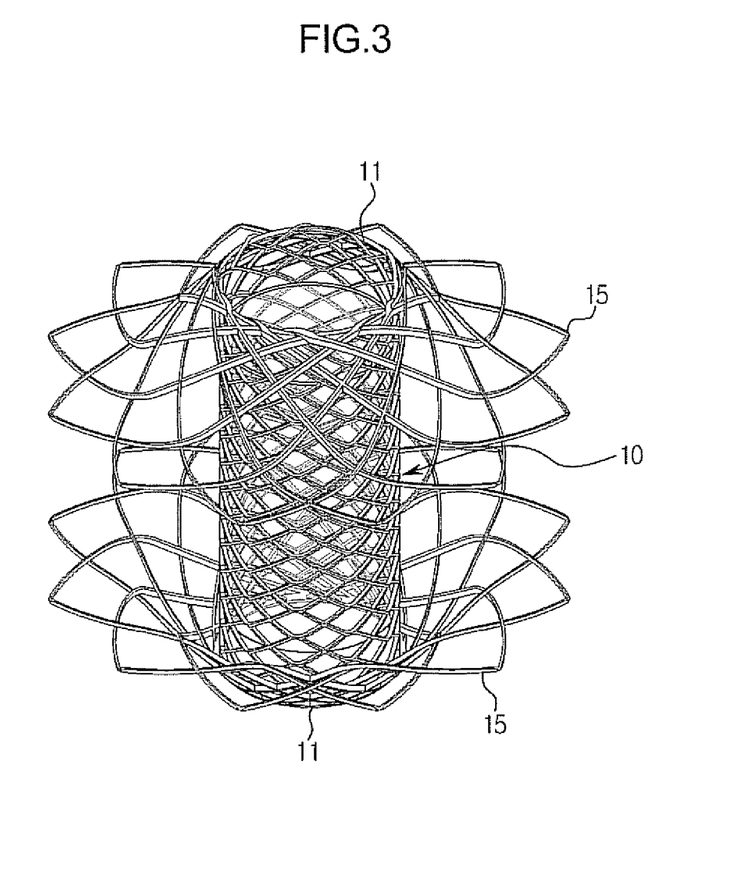
FIG. 3 is a diagram showing a perspective view of a stent, according to a preferred embodiment of the present invention.
Figure 4:
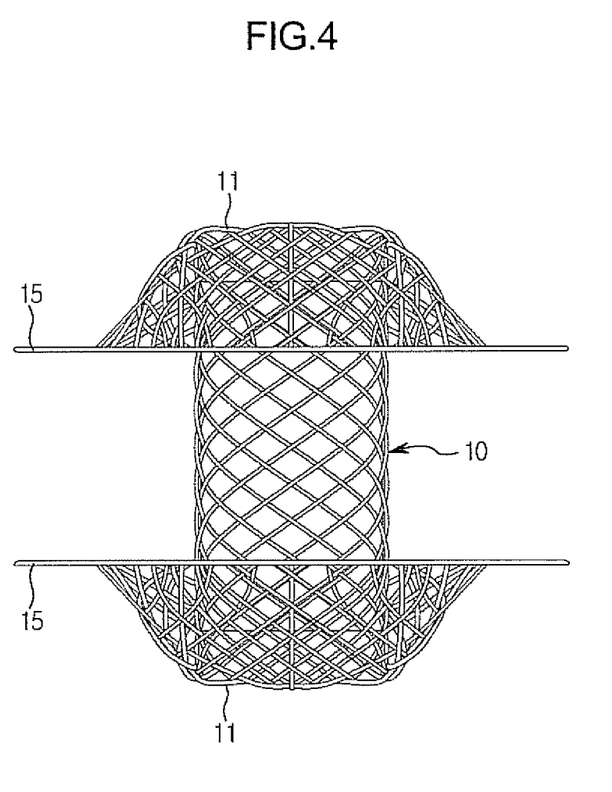
FIG. 4 is a diagram showing a side view of the stent of FIG. 3.
Figure 5:
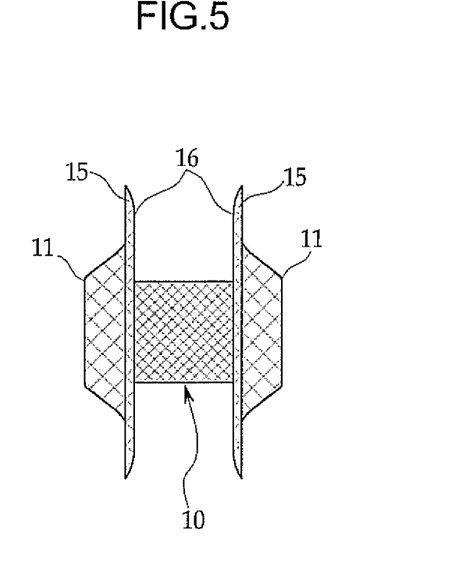
FIG. 5 is a side view of the stent of FIG. 3.
Figure 6:
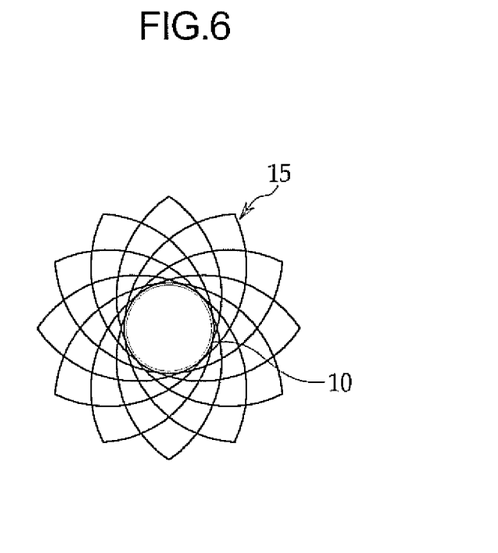
FIG. 6 is a front view of the stent of FIG. 5.
Figure 7:
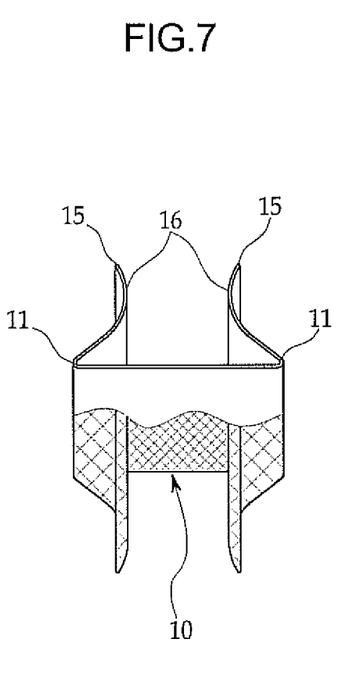
FIG. 7 is a partial side sectional view of the stent of FIG. 5.

FIG. 2 shows a stent which was proposed in US Patent 2009-281557 to overcome the problems of the stent of FIG. 1. In the stent of FIG. 2, a hollow cylindrical body 2 is formed by weaving an alloy wire such as a superelastic shape-memory alloy wire in a crossing manner. After the hollow cylindrical body 2 has been inserted into holes formed in the organs of a patient, increased diameter parts 4 are formed by pushing portions of opposite ends of the hollow cylindrical body 2 inwards with respect to the longitudinal direction so that the increased diameter parts 4 are locked to respective adjacent tissues 5, thus preventing the stent from being removed therefrom.

Although this stent can overcome the problem of the technique of FIG. 1 that makes it difficult to insert the stent into the holes in the tissues, because the distance between the increased diameter parts is also fixed, so that parts with an increased diameter must be formed to take into consideration the distance between adjacent tissues or the thicknesses of walls of the tissues. For these reasons, it is not easy to bring the parts with an increased diameter into elastic, close contact with the tissues so that a gap is formed between the stent and the tissues, making the discharge or shunting of bile or the like difficult.

SUMMARY OF THE INVENTION

Accordingly, the present invention has been made keeping in mind the above problems occurring in the prior art, and an object of the present invention is to provide a stent which includes a hollow cylindrical body formed by weaving a superelastic shape-memory alloy wire in an overlapping manner, and wing parts provided by expanding respective opposite ends of the hollow cylindrical body outwards and turning the opposite ends inside out on bent portions so that adjacent tissues of the organs, such as the gall bladder, the pancreas, etc., of a patient are supported by the wing parts, wherein the wing parts can elastically move inwards or outwards with respect to the longitudinal direction of the cylindrical body to automatically adjust the distance between the wing parts depending on the distance between the adjacent tissues of the organs or thicknesses of walls of the organs and to put them into close contact with the adjacent tissues of the organs, so that the stent can be used regardless of the distance between the adjacent tissues of the organs or the thicknesses of the tissues.

Another object of the present invention is to provide a stent which is configured such that the wing parts elastically move inwards or outwards in the longitudinal direction in response to the distance between the adjacent tissues of the organs or thicknesses of walls of the organs so that the wing parts can maintain the state of persistent, close contact with the tissues, whereby the fixation of the stent to the tissues and the function of preventing leaks thereof can be reliably ensured.

In order to accomplish the above object, the present invention provides a stent for connecting adjacent tissues of organs of a human body in such a way that the stent is inserted into holes made in the adjacent tissues and opposite ends thereof are supported on the respective adjacent tissues, the stent including: a hollow cylindrical body formed by weaving a superelastic shape-memory alloy wire in an overlapping manner such that a plurality of rhombic openings are formed; and wing parts provided by expanding respective opposite ends of the hollow cylindrical body outwards and turning the opposite ends inside out on bent portions, the wing parts facing each other so that the wing parts apply tension in a longitudinal direction of the hollow cylindrical body, whereby the wing parts elastically move inwards or outwards with respect to the longitudinal direction to automatically adjust a distance between the wing parts in response to the distance between the adjacent tissues of the organs or thicknesses of walls of the organs, so that the wing parts are put into close contact with the adjacent tissues of the organs.

The bent portion of each of the wing parts may be formed in a round shape.

An end of each of the wing parts may be bent outward to foam a round contact portion so that the round contact portion of the wing part is brought into close contact with the tissue of the corresponding organ, thus preventing the wing part from damaging the organ.

An artificial film may be applied to an outer surface of the cylindrical body or outer surfaces of the cylindrical body and the wing parts to isolate the inside thereof from the outside. The material artificial film may be PTFE or silicone that is friendly to the human body.

A stent according to the present invention connects adjacent tissues of the organs, such as the gall bladder, the pancreas, etc., of a patient so as to form a passage for an endoscopic operation or the like or for the discharge or shunting of bile or the like. For this, the stent of the present invention includes a hollow cylindrical body formed by weaving a superelastic shape-memory alloy wire in an overlapping manner, and wing parts provided by expanding respective opposite ends of the hollow cylindrical body outwards and turning the opposite ends inside out on bent portions so that adjacent tissues of the organs are supported by the wing parts. The wing parts can elastically move inwards or outwards with respect to the longitudinal direction of the cylindrical body to automatically adjust the distance between the wing parts depending on the distance between the adjacent tissues of the organs or thicknesses of walls of the organs and bring them into close contact with the adjacent tissues of the organs. Therefore, unlike the conventional technique, the stent of the present invention can be used regardless of the distance between the adjacent tissues of the organs or the thicknesses of the tissues. Moreover, because the stent can maintain the state of persistent, close contact with the tissues, the fixation of the stent to the tissues and the function thereof of preventing leaks can be reliably ensured.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, a preferred embodiment of the present invention will be described in detail with reference to the attached drawings.

A connection stent according to the present invention connects adjacent tissues of the organs, such as the gall bladder, pancreas, etc., of a patient in such a way that the adjacent tissues are pierced to form holes and the stent is inserted into the holes so that the tissues can communicate with each other, whereby a passage for an endoscopic operation or the like or for discharge or shunt of bile or the like is formed.

As shown in FIGS. 3 through 7, the connection stent according to the present invention includes a hollow cylindrical body 10 which is formed by weaving a superelastic shape-memory alloy wire in an overlapping manner such that a plurality of rhombic openings are formed, and wing parts 15 which are provided by expanding respective opposite ends of the hollow cylindrical body 10 outwards and turning them inside out on bent portions 11 to form a concave shape. The inside curvatures of the wing parts 15 directly face each other so that they wing parts 15 apply tension in the longitudinal direction of the hollow cylindrical body 10 having a center part which is positioned between the inside curvature of the concave shape of each wing part. The wing parts 15 can elastically move inwards or outwards with respect to the longitudinal direction to automatically adjust the distance of the center part between the wing parts 15 in response to the distance between the adjacent tissues of the organs of the patient or the thicknesses of the walls of the organs, so that the wing parts 15 can come into close contact with the adjacent tissues of the organs.

The bent portion 11 of each wing part 15 is bent to form a round surface. The bent portion 11 can elastically move in the longitudinal direction of the cylindrical body 10 until the rounded bent portion 11 reaches a yield point.

The end of each wing part 15 is bent outward to foam a round contact portion 16 so that the wing part 15 is brought into close contact with the tissue of the organ of the patient by the round contact portion 16, thus preventing the wing part 15 from damaging the organ.

An artificial film 30, the material of which is PTFE or silicone that is friendly to the human body, is applied to the outer surface of the cylindrical body 10 or both the cylindrical body 10 and the wing parts 15 to isolate the inside of the stent from the outside.

In the drawings, reference numeral 50 denotes a hole made in the organs of the patient, and reference numeral 100 and 200 respectively denote the organs of the patient.

The operation and effect of the stent of the present invention having the above-mentioned construction will now be described.

The stent of the present invention is inserted into the hole 50 that is made in the adjacent tissues of the organs 100 and 200, such as the gall bladder, pancreas, etc. to connect the organs 100 and 200 to each other so that they can communicate with each other.

Figure 10:
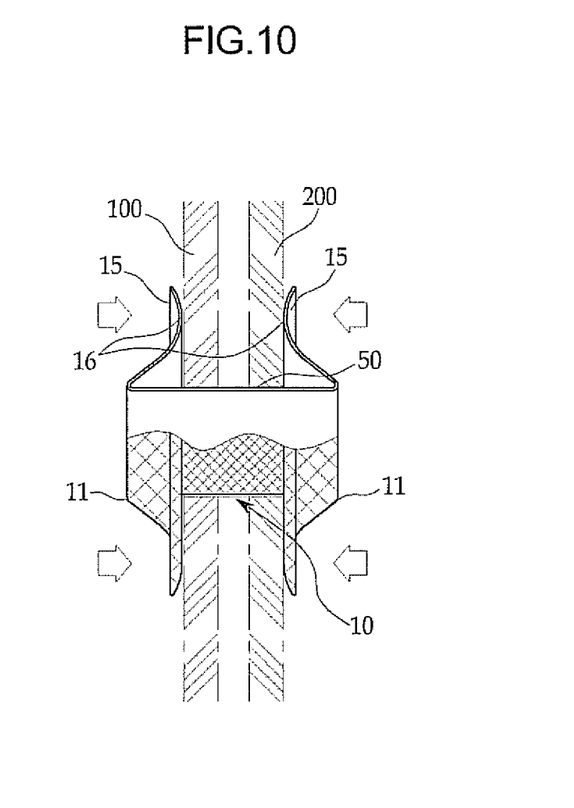
FIGS. 10 and 11 are side sectional views showing the installation of the stent of the present invention.
Figure 11:
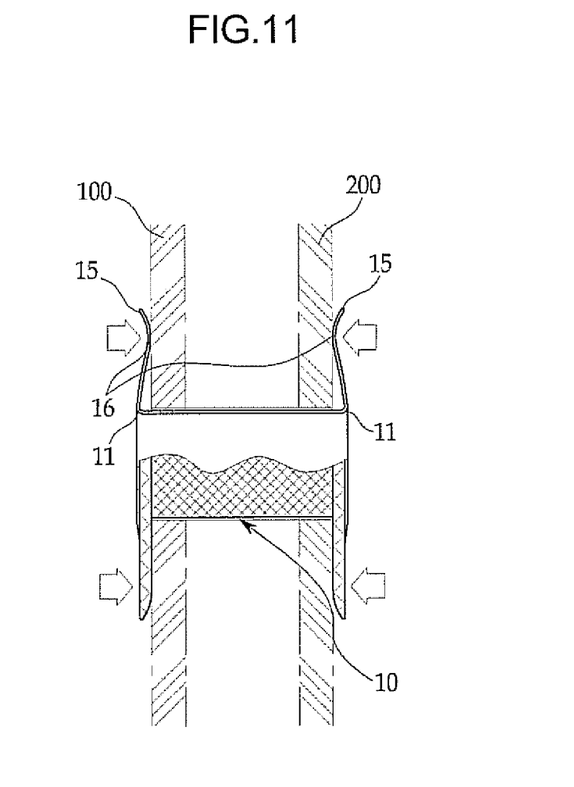

In other words, as shown in FIGS. 10 and 11, after the holes 50 are formed through portions of the organs 100 and 200 that are desired to communicate with each other, the stent of the present invention is inserted into the holes 50 by a separate stent insertion device. Here, the wing parts 15 that are provided on the opposite ends of the hollow cylindrical body 10 are elastically moved outwards with respect to the longitudinal direction to form a stretched shape, before inserting the stent into the holes 50 of the tissues. Thereafter, the wing parts 15 return to their original state, in other words, are elastically turned inside out on the bent portions 11, so that the wing parts 15 can elastically come into close contact with the surfaces of the tissues of the organs.

Particularly, because each wing part 15 can elastically move on the round bent portion 11 in the longitudinal direction of the cylindrical body 10 until the bent portion reaches the yield point, the wing parts 15 can be brought into close contact with the adjacent tissues of the organs while the distance between the wing parts 15 is automatically adjusted depending on the distance between the tissues of the organs or the thicknesses of the walls of the organs.

Furthermore, because the wing parts 15 that are provided on the opposite ends of the cylindrical body 10 elastically move in the longitudinal direction of the cylindrical body 10 in response to different distances between the adjacent tissues of the organs or the thicknesses of the walls of the organs and elastically come into close contact with the tissues, not only the fixation of the stent to the organs but a seal that prevents leaks can also be reliably ensured.

In addition, when the opposite wing parts 15 elastically are put into close contact with the adjacent tissues of the organs, the round contact portions 16, which are bent from the ends of the wing parts 15 outwards and are rounded, are put into contact with the tissues. Therefore, the wing parts 15 can be prevented from damaging the tissues.

As such, the stent of the present invention passes through the adjacent tissues of the organs and connects them to each other, thus forming a passage. Thus, when it is difficult to directly access a lesion in the organ, such as the gall bladder, the pancreas, etc., to conduct a surgical operation, for example, an endoscopic operation, the stent of the present invention enables the access to the lesion through the adjacent organ and allows the surgical operation to be conducted.

Figure 8:
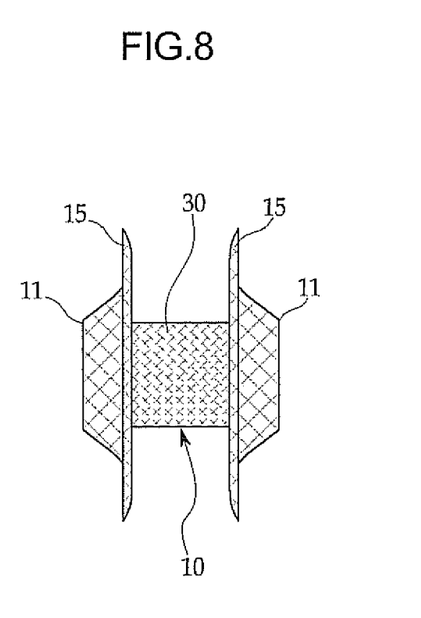
FIG. 8 is a side view showing another embodiment of the stent of FIG. 5.
Figure 9:
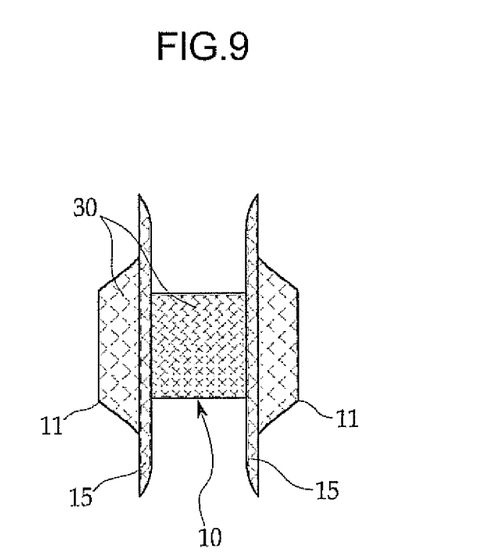
FIG. 9 is a side view showing a further embodiment of the stent of FIG. 5.

Further, the stent that connects the adjacent tissues of the organs and communicates them with each other may be used to discharge or shunt bile. In this case, as shown FIGS. 8 and 9, the artificial film 30, which is made of PTFE or silicone which is friendly to the human body, is applied to the outer surface of the cylindrical body 10 or both the cylindrical body 10 and the wing parts 15 so that the inside of the stent can be isolated from the outside.

As described above, a stent for connecting adjacent tissues of organs of a human body according to the present invention includes a hollow cylindrical body which is foiiued by weaving a superelastic shape-memory alloy wire in an overlapping manner, and wing parts which are formed by expanding respective opposite ends of the hollow cylindrical body outwards and turning them inside out on bent portions. The wing parts face each other such that they apply tension in the longitudinal direction of the hollow cylindrical body. Thus, the wing parts can elastically move inwards or outwards with respect to the longitudinal direction to automatically adjust the distance between the wing parts to suit the distance between the adjacent tissues of the organs of a patient or the thicknesses of the walls of the organs so that the wing parts can come into close contact with the adjacent tissues of the organs. Therefore, unlike the conventional technique, the stent of the present invention can be used regardless of the distances between the adjacent tissues of the organs or the thicknesses of the tissues. Moreover, the stent of the present invention can maintain a state of close contact with the adjacent tissues so that fixation of the stent and the function of preventing leaks can be reliably ensured.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A stent for providing fluidic coupling between adjacent tissues of organs of a human body, the stent comprising:
   a hollow cylindrical body woven from a super elastic shape memory alloy wire, the hollow cylindrical body having a center part, a first wing part and a second wing part,
   wherein each of the first wing part and the second wing part is formed by expanding a corresponding first end and a corresponding second end of the hollow cylindrical body outwards and turning the corresponding first end and the corresponding second end inside out at a corresponding first bent portion and a corresponding second bent portion to form a concave shape, so that an inside curvature of each of the concave shape of the first wing part and the concave shape of the second wing part directly face each other and the center part of the hollow cylindrical body is positioned between the inside curvatures of each concave shape of the wing parts,
   wherein each of the first wing part and the second wing part include a rounded convex contact edge formed substantially along a perimeter of the first wing part and the second wing part so that an inside curvature of the rounded convex contact edge of the first wing part and an inside curvature of the rounded convex contact edge of the second wing part face away from each other in opposing directions,
   wherein a distal edge of each of the first and second wing parts are bent away from a plane between the first and second wing parts perpendicular to a longitudinal axis of the hollow cylindrical body and the rounded convex contact edges of the first wing part and the second wing part are capable of contacting the tissue of the organs to prevent each wing part from damaging the tissues of the organs,
   wherein the first and second wing parts apply tension in a longitudinal direction of the hollow cylindrical body and can elastically move inwards or outwards respectively in the longitudinal direction such that during inward and outward movements a length of the center part between the first and second wing parts decreases and increases respectively, thereby automatically adjusting a distance between the first wing part and the second wing part, based on a distance between the adjacent tissues of the organs or thicknesses of walls of the organs; and a passage formed by an interior of the center part having a common axis with the hollow cylindrical body and each wing part, and positioned between the corresponding first bent portion and the corresponding second bent portion such that when the first wing part moves inwards to or outwards from the second wing part in an longitudinal direction or the second wing part moves inwards or outwards from the first wing part in the longitudinal direction, the passage of the center part of the hollow cylindrical body remains hollow.

2. The stent as set forth in claim 1, wherein the corresponding first bent portion and the corresponding second bent portion is formed in a round shape.

3. The stent as set forth in claim 2, wherein the first and second wing parts are able to elastically move in the longitudinal direction of the hollow cylindrical body while maintaining the center part of the hollow cylindrical body hollow until the corresponding first and second bent portions reach yield points.

4. The stent as set forth in claim 1, wherein the first and second wing parts are able to elastically move in the longitudinal direction of the hollow cylindrical body while maintaining the center part of the hollow cylindrical body hollow until the corresponding first and second bent portions reach yield points.

5. The stent as set forth in claim 1, wherein an artificial film is applied to an outer surface of the hollow cylindrical body to isolate an inside thereof from an outside thereof.

6. The stent as set forth in claim 1, wherein an artificial film is applied to outer surfaces of the hollow cylindrical body and the first and second wing parts to isolate an inside thereof from an outside thereof.

* * * * *

UNITED STATES PATENT AND TRADEMARK OFFICE
CERTIFICATE OF CORRECTION

PATENT NO. : 9,668,853 B2  
APPLICATION NO. : 13/542412  
DATED : June 6, 2017  
INVENTOR(S) : Kyong-Min Shin Page 1 of 1

It is certified that error appears in the above-identified patent and that said Letters Patent is hereby corrected as shown below:

On the Title Page

Add the Inventor as follows:
(75) Inventor: JONG HO MOON, Seoul (KR)
Address: #402 HyoWon Villat, 135-6 Mok-Dong, YangChun-Ku, Seoul 07969, KOREA Signed and Sealed this
First Day of February, 2022

Drew Hirshfeld
*Performing the Functions and Duties of the*
*Under Secretary of Commerce for Intellectual Property and*
*Director of the United States Patent and Trademark Office*